United States Patent

Audiau et al.

[11] Patent Number: 5,403,837
[45] Date of Patent: Apr. 4, 1995

[54] 1,2,4-THIADIAZINO[3,4-B]BENZO-THIAZOLE DERIVATIVES, AND MEDICINAL PRODUCTS CONTAINING THEM

[75] Inventors: Francois Audiau, Charenton Le Pont; Patrick Jimonet, Villepreux; Serge Mignani, Chatenay Malabry, all of France

[73] Assignee: Rhone Poulenc Rorer S.A., Antony Cedex, France

[21] Appl. No.: 157,087

[22] PCT Filed: Jun. 30, 1992

[86] PCT No.: PCT/FR92/00611
§ 371 Date: Dec. 7, 1993
§ 102(e) Date: Dec. 7, 1993

[87] PCT Pub. No.: WO93/01194
PCT Pub. Date: Jan. 21, 1993

[30] Foreign Application Priority Data
Jul. 4, 1991 [FR] France .................. 91 08354

[51] Int. Cl.⁶ ............... A61K 31/54; C07D 513/04
[52] U.S. Cl. ............................. 514/222.8; 544/9
[58] Field of Search .................. 544/9; 514/222.8

[56] References Cited
FOREIGN PATENT DOCUMENTS
0374040 6/1990 European Pat. Off. .
0375510 7/1990 European Pat. Off. .
0409692 1/1991 European Pat. Off. .

OTHER PUBLICATIONS

Krutak et al, Chemical Abstract, vol. 91, entry 192232a (1979).
Journal of Organic Chemistry, vol. 44, No. 22, (1979), pp. 3847–3858, J. J. Krutak et al., 'Chemistry of Ethenesulfonyl Fluoride.
Chemische Berichte, vol. 100, pp. 2159–2163, H. Beecken 'Über die Cycloaddition heterocyclisher N-sulfinyl–amine an Bicyclo[2.2.1]hepten und Äthoxyacetylen' (1967).

Primary Examiner—John M. Ford
Attorney, Agent, or Firm—Morgan & Finnegan

[57] ABSTRACT

This invention relates to compounds of formula (I):

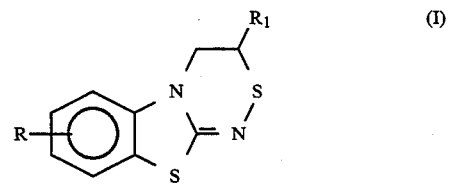

wherein R is a polyfluoroalkoxy, polyfluoroalkyl, alkoxy or alkyl radical and $R_1$ is a hydrogen atom or an alkyl radical; salts thereof; the preparation thereof; and drugs containing same.

8 Claims, No Drawings

1,2,4-THIADIAZINO[3,4-B]BENZOTHIAZOLE DERIVATIVES, AND MEDICINAL PRODUCTS CONTAINING THEM

DESCRIPTION OF THE INVENTION

The present invention relates to derivatives of formula:

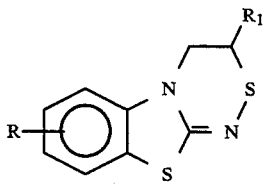

their salts, their preparation and medicinal products containing them.

Patent EP 374040 describes 2-iminobenzothiazoline derivatives which are active towards glutamate-induced convulsions.

In the formula (I),

R represents a polyfluoroalkoxy, polyfluoroalkyl, alkoxy or alkyl radical, $R_1$ represents a hydrogen atom or an alkyl radical.

In the above definitions and in those which will be mentioned below, the alkyl and alkoxy radicals and portions contain 1 to 4 carbon atoms in a linear or branched chain.

The polyfluoroalkyl radicals are preferably trifluoromethyl, 2,2,2-trifluoroethyl and pentafluoroethyl radicals.

The polyfluoroalkoxy radicals are preferably trifluoromethoxy, pentafluoroethoxy, 2,2,2-trifluoroethoxy and 1,1,2,2-tetrafluoroethoxy radicals.

The invention also relates to the addition salts of the compounds of formula (I) with inorganic or organic acids.

The compounds of formula (I) may be prepared by cyclisation of a derivative of formula:

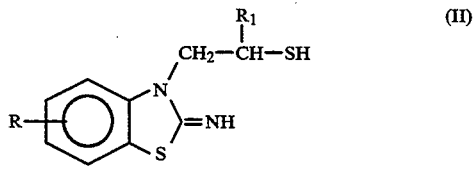

in which R and $R_1$ have the same meanings as in the formula (I).

This cyclisation is generally carried out in an oxidizing medium (for example bromine, chlorine, iodine, potassium triiodide, hydrogen peroxide or chloramine-T) in an inert solvent such as an alcohol (for example methanol or ethanol), a chlorine-containing solvent (for example chloroform or methylene chloride), an aromatic solvent (for example benzene or toluene), or a ketone (for example acetone), at a temperature ranging from 20° to 50° C.

The derivatives of formula (II) may be obtained by hydrolysis of a derivative of formula:

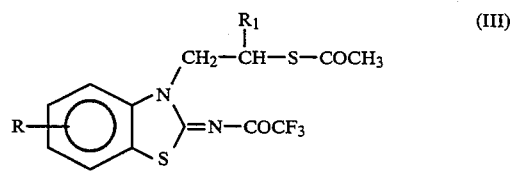

in which R and $R_1$ have the same meanings as in the formula (I).

This hydrolysis is preferably carried out by means of a base such as an alkali metal carbonate (for example sodium or potassium), or an alkali metal hydroxide (for example sodium hydroxide or potassium hydroxide), in an inert solvent such as an alcohol, a ketone, water or a mixture of these solvents, at a temperature of between 20° and 50° C.

The derivatives of formula (III) may be obtained by reacting thioacetic acid with a derivative of formula:

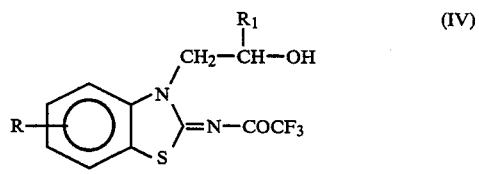

in which R and $R_1$ have the same meanings as in the formula (I).

This reaction is preferably carried out in an inert solvent such as tetrahydrofuran, by means of triphenylphosphine and ethyl azodicarboxylate, at a temperature of between 0° and 25° C.

The derivatives of formula (IV) may be prepared by applying or adapting the method described in Patent EP409692.

The reaction mixtures obtained by the various methods described above are treated using conventional physical methods (evaporation, extraction, distillation, chromatography, crystallization and the like) or conventional chemical methods (formation of salts and the like).

The compounds of formula (I), in the form of a free base, may be optionally converted to the addition salts with an inorganic or organic acid, by reaction of such an acid in an organic solvent such as an alcohol, a ketone, an ether or a chlorine-containing solvent.

The compounds of formula (I) and their salts possess advantageous pharmacological properties. These compounds interfere with glutamatergic transmission and are therefore useful in the treatment and prevention of phenomena linked to glutamate. These phenomena are in particular epileptogenic and/or convulsive manifestations, schizophrenic disorders and in particular the deficiency forms of schizophrenia, sleep disorders, anxiety, phenomena linked to cerebral ischaemia as well as neurological disorders linked to aging where glutamate may be involved, such as Alzheimer's disease, Huntington's disease, amyotrophic lateral sclerosis and olivopontocerebellar atrophy.

The antiglutamate activity of these products has been determined for convulsions induced by glutamate according to a technique inspired by that of I. P. LAPIN, J. Neural. Transmission, 54, 229–238 (1982); the injection of glutamate by the intracerobroventricular route being carried out according to a technique inspired by that of R. CHERMAT and P. SIMON, J. Pharmacol. (Paris), 6, 489–492 (1975). Their $ED_{50}$ is less than or equal to 10 mg/kg.

The compounds of formula (I) are of low toxicity. Their $LD_{50}$ is greater than 15 mg/kg by the IP route in mice.

For medicinal use, the compounds of formula (I) may be used as they are or in the form of pharmaceutically acceptable salts, that is to say nontoxic at the applied doses.

The addition salts with inorganic or organic acids, such as acetate, propionate, succinate, benzoate, fumarate, maleate, oxalate, methanesulphonate, isethionate, theophyllinacetate, salicylate, methylene-bis-$\beta$-oxynaphthoate, hydrochloride, sulphate, nitrate and phosphate, may be mentioned as examples of pharmaceutically acceptable salts.

The following example, which is given with no limitation being implied, shows how the invention may be implemented in practice.

EXAMPLES

Example 1

1.2 g of 2-imino-3-(2-mercaptoethyl)-6-trifluoromethoxybenzothiazoline are added gradually to 1.2 g of chloramine-T trihydrate (Prolabo) in solution in 15 cm³ of methanol, at a temperature of about 20° C. The reaction is continued for 2 hours at this temperature. The methanol is evaporated under reduced pressure and the whitish residue is taken up in 50 cm³ of distilled water. The organic phase is extracted twice with 30 cm³ of ethyl ether, washed with distilled water and then dried over magnesium sulphate. After filtration and concentration to dryness under reduced pressure, 1.2 g of a white foam are obtained which are purified by flash chromatography on silica, using an ethyl acetate-cyclohexane mixture (40–60 by volume) as eluent. 0.9 g of 3,4-dihydro-8-trifluoro-methoxy-1,2,4-thiadiazino[3,4-b]benzothiazole is obtained in the form of a colourless oil which, with the addition of oxalic acid in acetone, gives 0.8 g of oxalate; melting point 178° C.

2-Imino-3-(2-mercaptoethyl)6-trifluoromethoxybenzothiazoline may be prepared in the following manner: 75 cm³ of a solution of 7% potassium carbonate in water are added to 15.1 g of 3-(2-acetylthioethyl)-2-trifluoroacetylimino-6-trifluoromethoxybenzothiazoline in solution in 500 cm³ of methanol, at a temperature of about 20° C. After reacting at this temperature for 72 hours, the methanol is evaporated under reduced pressure and the solid residue is taken up in 500 cm³ of distilled water. The white insoluble matter is filtered, washed with water and then dried. After purification by flash chromatography on a silica column using ethyl acetate as eluent, 6.3 g of 2-imino-3-(2-mercaptoethyl)-6-trifluoromethoxybenzothiazoline are obtained in the form of a white solid; melting point 110° C.

3-(2-Acetylthioethyl)-2-trifluoroacetylimino-6-trifluoromethoxybenzothiazoline may be obtained in the following manner: 21 g of triphenylphosphine and 150 cm³ of tetrahydrofuran are introduced into a round bottom flask placed under nitrogen. A solution of 12.8 cm³ of ethyl azodicarboxylate in 100 cm³ of tetrahydrofuran is added dropwise, over about 30 minutes, to this mixture, stirred at 0°–5° C. The stirring is continued at this temperature for 1 hour. A solution of 14.2 g of 3-(2-hydroxyethyl)-2-trifluoroacetylimino-6-trifluoromethoxy-benzothiazoline and 5.6 cm³ of thioacetic acid in 250 cm³ of tetrahydrofuran is then added dropwise over about 30 minutes at 0° C. This temperature is maintained for 1 hour and the reaction is then continued for 15 hours at a temperature of about 20° C. After concentration to dryness under reduced pressure, the residue is purified by flash chromatography on a silica column, using a cyclohexane-ethyl acetate mixture (95–5 by volume) as eluent. 15.3 g of expected product are thus obtained in the form of a white powder; melting point 120° C.

3-(2-Hydroxyethyl)-2-trifluoroacetylimino-6-trifluoromethoxybenzothiazoline may be prepared according to the method described in Patent EP 409692.

The medicinal products according to the invention consist of a compound of formula (I) in free form or in the form of an addition salt with a pharmaceutically acceptable acid, in the pure state or in the form of a composition in which it is combined with any other pharmaceutically compatible product which may be inert or physiologically active. The medicinal products according to the invention may be used orally, parenterally, intravenously, rectally or topically.

Tablets, pills, powders (gelatin capsules, cachets) or granules may be used as solid compositions for oral administration. In these compositions, the active ingredient according to the invention is mixed with one or more inert diluents such as starch, cellulose, sucrose, lactose or silica under an argon stream. These compositions may also comprise substances other than diluents, for example one or more lubricants such as magnesium stearate or talc, a colorant, a coating (sugared pills) or a varnish.

Pharmaceutically acceptable solutions, suspensions, emulsions, syrups and elixirs containing inert diluents such as water, ethanol, glycerol, vegetable oils or paraffin oil may be used as liquid compositions for oral administration. These compositions may comprise substances other than diluents, for example wetting, sweetening, thickening, flavouring or stabilizing products.

The sterile compositions for parenteral administration may be preferably aqueous or nonaqueous solutions, suspensions or emulsions. Water, propylene glycol, polyethylene glycol, vegetable oils, in particular olive oil, organic esters for injection, for example ethyl oleate, or other suitable organic solvents may be used as solvent or vehicle. These compositions may also contain adjuvants, in particular wetting, isotonizing, emulsifying, dispersing and stabilizing agents. Sterilization may be performed in a number of ways, for example by aseptizing filtration, by incorporating sterilizing agents into the composition, by irradiation or by heating. They may also be prepared in the form of sterile solid compositions which may be dissolved at the time of use in sterile water or in any other sterile medium for injection.

The compositions for rectal administration are suppositories or rectal capsules which contain, in addition to the active product, excipients such as cocoa butter, semisynthetic glycerides or polyethylene glycols.

The compositions for topical administration may be for example creams, lotions, collyria, collutories, nasal drops or aerosols.

In human therapy, the compounds according to the invention interfere with glutamatergic transmission and are therefore particularly useful in the treatment and prevention of disorders linked to glutamate. These compounds are in particular useful for the treatment or prevention of epileptogenic and/or convulsive manifestations, schizophrenic disorders and in particular the deficiency forms of schizophrenia, sleep disorders, anxiety, phenomena linked to cerebral ischaemia as well as neurological disorders linked to aging where glutamate may be involved, such as Alzheimer's disease, Huntington's disease, amyotrophic lateral sclerosis and olivopontocerebellar atrophy.

The doses depend on the desired effect, on the duration of treatment and on the administration route used; they are generally between 30 and 300 mg per day orally for an adult with unit doses ranging from 10 mg to 100 mg of active substance.

Generally, the physician will determine the appropriate dosage according to the age, the weight and all the other factors which are specific to the individual to be treated.

The following examples illustrate compositions according to the invention:

EXAMPLE A

Gelatin capsules containing a dose of 50 mg of active product and having the following composition are prepared using the usual technique:

| | |
|---|---|
| 3,4-Dihydro-8-trifluoromethoxy-1,2,4-thiadiazino[3,4-b]benzothiazole | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

EXAMPLE B

Tablets containing a dose of 50 mg of active product and having the following composition are prepared using the usual technique:

| | |
|---|---|
| 3,4-dihydro-8-trifluoromethoxy-1,2,4-thiadiazino[3,4-b]benzothiazole | 50 mg |
| Lactose | 104 mg |
| Cellulose | 40 mg |
| Polyvidone | 10 mg |
| Carboxymethylstarch sodium | 22 mg |
| Talc | 10 mg |
| Magnesium stearate | 2 mg |
| Colloidal silica | 2 mg |
| Mixture of hydroxymethylcellulose glycerine, titanium oxide (72-3.5-24.5) qs 1 finished coated tablet of | 245 mg |

EXAMPLE C

A solution for injection containing 10 mg of active product and having the following composition is prepared:

| | |
|---|---|
| 3,4-Dihydro-8-trifluoromethoxy-1,2,4-thiadiazino[3,4-b]benzothiazole | 10 mg |
| Benzoic acid | 80 mg |
| Benzyl alcohol | 0.06 cm$^3$ |
| Sodium benzoate | 80 mg |
| Ethanol, 95% | 0.4 cm$^3$ |
| Sodium hydroxide | 24 mg |
| Propylene glycol | 1.6 cm$^3$ |
| Water qs | 4 cm$^3$ |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are there hereby incorporated by reference.

It is claimed:

1. A compound of formula:

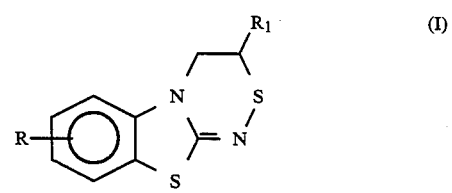

in which R represents a polyfluoroalkoxy, polyfluoroalkyl, alkoxy or alkyl radical, and R$_1$ represents a hydrogen atom or an alkyl radical, and their salts with an inorganic or organic acid, it being understood that the alkyl radicals and portions and the alkoxy portions contain 1 to 4 carbon atoms in a linear or branched chain.

2. A compound of formula (I) according to claim 1, wherein R represents a trifluoromethyl, 2,2,2 - trifluoroethyl, trifluoromethoxy, pentafluoroethyl, 2,2,2 - trifluoroethoxy or 1,1,2,2 - tetrafluoroethoxy radical.

3. 3,4 -Dihydro- 8 - trifluoromethoxy-1,2,4-thiadiazino[3,4-b]benzothiazole and its salts with an inorganic or organic acid.

4. Method of preparing compounds of formula (I) according to claim 1, comprising cyclizing in an oxidizing medium a derivative of formula:

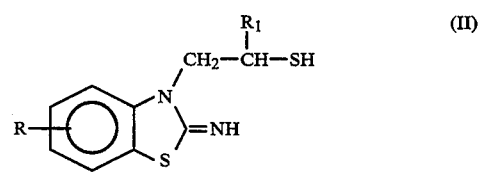

in which R and R$_1$ have the same meaning as in claim 1.

5. A pharmaceutical composition which comprises, as active principle, at least one compound according to claim 1, or a salt of such a compound with an inorganic or organic acid and a compatible pharmaceutically acceptable carrier.

6. A pharmaceutical composition which comprises, as active principle, at least one compound according to claim 2, or a salt of such a compound with an inorganic or organic acid an a compatible pharmaceutically acceptable carrier.

7. A pharmaceutical composition which comprises, as active principle, 3,4-dihydro-8-trifluoromethoxy-1,2,4-thiadiazino[3,4-b]benzothiazole or a salt of this compound with an inorganic or organic acid and a compatible pharmaceutically acceptable carrier.

8. A method for the treatment of a medical condition associated with the effects of glutamate which comprises administering to a subject in need of such treatment an amount of a compound according to claim 1 or a salt thereof sufficient to inhibit such effects.

* * * * *